(12) United States Patent
Sulzer et al.

(10) Patent No.: US 8,021,646 B2
(45) Date of Patent: Sep. 20, 2011

(54) COMPOSITIONS AND METHODS FOR MAGNETIC RESONANCE IMAGING CONTRAST AGENTS

(75) Inventors: Lindsay K. Sulzer, Chicago, IL (US); Steven R. Bull, Boston, MA (US); Annelise Emily Barron, Palo Alto, CA (US); Thomas J Meade, Wilmette, IL (US)

(73) Assignee: Northwestern University, Evanston, IL (US)

( * ) Notice: Subject to any disclaimer, the term of this patent is extended or adjusted under 35 U.S.C. 154(b) by 864 days.

(21) Appl. No.: 11/952,691

(22) Filed: Dec. 7, 2007

(65) Prior Publication Data

US 2009/0053141 A1 Feb. 26, 2009

Related U.S. Application Data

(60) Provisional application No. 60/873,908, filed on Dec. 8, 2006.

(51) Int. Cl.
*A61B 5/055* (2006.01)

(52) U.S. Cl. ........... 424/9.36; 424/1.11; 424/1.69; 424/9.1; 424/9.3; 530/328

(58) Field of Classification Search ........... 424/1.11, 424/1.49, 1.65, 1.69, 1.73, 9.1, 9.2, 9.3, 9.32, 424/9.321, 9.322, 9.323, 9.34, 9.341, 9.35, 424/9.351, 9.36, 9.361, 9.362, 9.364; 534/7, 534/10–16; 530/328
See application file for complete search history.

(56) References Cited

U.S. PATENT DOCUMENTS 6,998,115 B2   2/2006   Langer
7,642,239 B2 * 1/2010   Taylor et al. ............ 514/1.1

OTHER PUBLICATIONS

Cherry, 2004, Phy. In Med. Biol. 49:R13-48.
Won and Barron, 2002, Macromol. 35:8281-8287.
Artemov et al., 2004, Curr.Pharm. Biotech. 5:485-494.
Wang et al., 2004, Pharm. Res. 22:596-602.
Wen et al., 2004, Bioconj. Chem. 15:1408-1415.
Lee et al., 2005, J. Am. Chem. Soc. 127:13164-13166.
Caravan et al., 1999, Chem. Rev. 99:2293-2352.
Opsahl et al., 1995, Acad. Rad. 2:762-767.
Desser et al., 1994, J. Mag. Res. Imaging 4:467-472.
Kobayashi and Brechbiel, 2005, Ad. Drug Dei. Rev. 57:2271-2286.
Langereis et al., 2006, NMR in Biomed. 19:133-141.
Sirlin et al., 2004, Acad. Rad. 11: 1361.
Huber et al., 1998, Bioconj. Chem. 9:242-249.
Langereis et al., 2004, Org. Bio. Chem. 2:1271-1273.
Shahbazi-Gahrouei et al., 2001, J. Mag. Res. Imaging 14:169-174.
Strijkers et al., 2005, Magma 18:186-192.
Lanza et al., 2004, Curr. Pharma. Biotech. 5:495-507.
Lu et al., 2003, Mag. Res. Med. 51:27-34.
Mohs et al., 2004, Bioconj. Chem. 15:1424-1430.
Zong et al., 2005, Meg. Res. Med. 53:835-842.
Cheng et al., 2005, J. Mag. Res. Imaging 21:415-423.
Neves et al., 2006, Tissue Eng. 12:53-62.
Barbash et al., 2004, Heart 90:87-91.
Stroman et al., 1999, Mag. Res. Med. 42:210-214.
Guidoin et al., 2004, Art. Cells, Blood Subs., Imm. Biotech. 32:105-127.
Pihlajamaki et al., 1997, Biomat. 18:1311-1315.
Bull et al., 2005, Bioconj. Chern. 16:1343-1348.
Bull et al., 2005. Nano Lett. 5:1-4.
Morawski et al., 2005, Curr. Opin. Biotech. 16:89-92.
Mulder et al., 2005, FASEB J. 19:2008-2010.
Mitchell et al., 2000, J. Peptide Res. 56:318-325.
Wunderbaldinger et al., 2002, Bioconj. Chem. 13:264-268.
Allen and Meade, 2003, J. Biol. Inorg. Chern. 8:746-750.
Allen et al., 2004, "Cellular Delivery of MRI Contrast Agents." Chem. Biol. 11:301-307.

\* cited by examiner

*Primary Examiner* — Dameron Levest Jones
(74) *Attorney, Agent, or Firm* — Casimir Jones, S.C.

(57) ABSTRACT

The present application provides for compositions and methods of creating and applying contrast agents that find use in magnetic resonance imaging (MRI). In particular, contrast agents that comprise monodisperse, protein polymer backbones capable of chelating multiple paramagnetic ions resulting in high relaxivity for use in enhancing MRI signal intensity.

19 Claims, 8 Drawing Sheets

```
                        SEQUENCE LISTING

<160> NUMBER OF SEQ ID NOS: 9

<210> SEQ ID NO 1
    <211> LENGTH: 8
    <212> TYPE: PRT
    <213> ORGANISM: Artificial Sequence
    <220> FEATURE:
    <223> OTHER INFORMATION: Synthetic

<400> SEQUENCE: 1

Gly Lys Ala Gly Thr Gly Ser Ala
    1               5

<210> SEQ ID NO 2
    <211> LENGTH: 30
    <212> TYPE: PRT
    <213> ORGANISM: Artificial Sequence
    <220> FEATURE:
    <223> OTHER INFORMATION: Synthetic

<400> SEQUENCE: 2

Ala Gln Leu Glu Lys Glu Leu Gln Ala Leu Glu Lys Glu Leu Ala Gln
    1               5                   10                  15

Leu Glu Trp Glx Leu Gln Ala Leu Glu Lys Glu Leu Ala Gln
                20                  25                  30

<210> SEQ ID NO 3
    <211> LENGTH: 30
    <212> TYPE: PRT
    <213> ORGANISM: Artificial Sequence
    <220> FEATURE:
    <223> OTHER INFORMATION: Synthetic

<400> SEQUENCE: 3

Ala Gln Leu Lys Lys Lys Leu Gln Ala Leu Lys Lys Lys Leu Ala Gln
    1               5                   10                  15

Leu Lys Trp Lys Leu Gln Ala Leu Lys Lys Lys Leu Ala Gln
                20                  25                  30

<210> SEQ ID NO 4
    <211> LENGTH: 9
    <212> TYPE: PRT
    <213> ORGANISM: Artificial Sequence
    <220> FEATURE:
    <223> OTHER INFORMATION: Synthetic

<400> SEQUENCE: 4

Gly Phe Lys Ala Gly Thr Gly Ser Ala
    1               5

<210> SEQ ID NO 5
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 5

Gly Arg Lys Lys Arg Arg Gln Arg Arg Arg
1               5                   10

<210> SEQ ID NO 6
<211> LENGTH: 23
<212> TYPE: PRT
<213> ORGANISM: Artificial Sequence
<220> FEATURE:
<223> OTHER INFORMATION: Synthetic

<400> SEQUENCE: 6

Gly His His His His His His His His Ser Ser Gly His Ile
1               5                   10                  15

Asp Asp Asp Asp Lys His Met
            20

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Gly Gln Gln Gln Leu Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Gly Lys Gly Thr Gly Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Lys Gly Ser Gly Lys Gly Ala
1               5
```

COMPOSITIONS AND METHODS FOR MAGNETIC RESONANCE IMAGING CONTRAST AGENTS

CROSS REFERENCE TO RELATED APPLICATION

The present application claims priority to the U.S. Provisional Patent Application No. 60/873,908 filed Dec. 8, 2006, incorporated herein by reference in its entirety.

STATEMENT REGARDING FEDERALLY SPONSORED RESEARCH OR DEVELOPMENT

This invention was made with government support under Grant Numbers: CA005024; CA199341; EB003806; and EB005866 awarded by the National Institutes of Health. The government has certain rights in the invention.

FIELD OF THE INVENTION

The present application provides for compositions and methods of contrast agents that find use in magnetic resonance imaging (MRI). In particular, contrast agents that comprise monodisperse, protein polymer backbones capable of chelating multiple paramagnetic ions resulting in high relaxivity for use in enhancing MRI signal intensity.

BACKGROUND OF THE INVENTION

Magnetic resonance imaging (MRI) has emerged as a very important technique in medical diagnostics and more recently in the study of complex biological processes such as gene expression (Cheery, 2004, Phy. In Med. Biol. 49:R13-48). Magnetic resonance imaging affords many unique advantages because it provides data in four dimensions (x, y and z axis, and time) and also permits non-invasive imaging of whole animals. One limitation of MRI, however, is its relatively low sensitivity, which is typically addressed with the use of contrast agents (CAs). Current clinically used CAs are small molecules, typically paramagnetic ions (e.g., gadolinium(III)) chelated by small organic molecules, and are used as blood pool agents that are excreted from the body in less than an hour. Recent research has turned toward synthetic polymers to increase the blood retention time of CAs, but such polymers are generally polydisperse and hence difficult to characterize and control (Huber et. al., 1998, Conj. Chem. 9:242-249; Watanabe, 2002, Mag. Res. Med. Sci. 1:38-49).

With increasing focus on earlier detection of disease, MRI is poised to play an important role in predictive and preventative medicine. Magnetic resonance imaging non-invasively provides three-dimensional visualization of whole tissues as well as molecular targets and processes at cellular resolution (~10 μm) (Huber et al., 1998). For example, the progression of tumors can be assessed through MRI by detection of tumor vascular permeability measurements (Wen et al., 2004, Bioconj. Chem. 15:1408-1415). Besides screening and staging of disease, MRI can also be used to select and optimize therapy (Artemov et al., 2004, Curr. Pharm. Biotech. 5:485-494).

In addition to improving medical diagnostics and therapeutics, MRI has great potential for enabling new discoveries in cellular and molecular biology. The imaging of gene expression commonly uses an optically visible reporter that is co-expressed with the gene of interest. In order to analyze the reporter, these methods often require killing the animal and fixing the tissue for histochemical detection (Genove et al., 2005, Nat. Med. 11:450-454). Magnetic resonance imaging also has significant advantages over other techniques in detecting cell signaling. Light microscopy, the most popular method of imaging cell signaling, is limited by light scattering, often produces photobleaching byproducts, and is also invasive (Lee et al., 2005, J. Am. Chem. Soc. 127:13164-13166). Imaging techniques such as PET and SPECT require the use of radioactive tracers and additionally are limited by low spatial resolution (Artemov et al., 2004). By preserving the animal, MRI allows for the examination of complex biological processes over time and in a variety of conditions.

Magnetic resonance imaging takes advantage of the interaction between an applied magnetic field and the nuclear spin of hydrogen protons (Brown and Semelka, 2003, *MRI: Basic Principles and Applications*, 3$^{rd}$ ed., John Wiley & Sons, Inc, Hoboken, N.J.). Instruments used for MRI measure variations in the excitation (or relaxation) of protons associated with water molecules to produce an image, the intensity of which is related to water concentration and the rate of relaxation of proton spins. The relaxation time $T_1$, the spin-lattice relaxation time, is a measure of how quickly protons release energy to the surroundings following an excitation pulse (Brown and Semelka, 2003). The spin-spin relaxation time, $T_2$, is the time for proton-proton energy transfer. A shorter $T_1$ relaxation time leads to a stronger net magnetization of the protons, providing a higher intensity signal. On the other hand, faster $T_2$ relaxation dephases the nearby water protons more than the surrounding tissue, resulting in signal loss and better negative contrast (Brown and Semelka, 2003).

The primary limitation of MRI is the lack of sufficient contrast difference between the water proton signal in the area of interest and the surrounding tissues. To overcome this problem, contrast agents are employed to increase the relaxation difference. Contrast agents ($T_1$) provide positive contrast enhancement by employing paramagnetic ions, such as gadolinium (III) (Gd (III)), manganese (II) (Mn(II)), and iron (III) (Fe(III)) (Artemov et al., 2004). These ions have a high magnetic moment because of their large number of unpaired electrons, and can speed up the energy transfer to produce a faster relaxation rate. In currently used $T_1$ contrast agents, a paramagnetic ion, which is toxic on its own, is chelated by small organic molecules such as diethylenetriaminepentaacetic acid (DTPA) and 1,4,7,10-tetraazacyclododecome-1,4,7,10-tetraacetic acid (DOTA) (Wang et al., 2004, Pharm. Res. 22:596-602). Magnevist™ and Omniscan™ are two frequently used commercial products for MRI that contain Gd(III) chelated by DTPA (Artemov et al., 2004). However, these low-molecular weight agents not only have low retention times in vivo, but they also provide insufficient contrast to allow MRI methods to be applied in all of the potential medical diagnostic and biological research applications which are of interest.

Macromolecular scaffolds for the display of multiple Gd(III) chelating moieties have been used to improve the performance of contrast agents. By coupling multiple paramagnetic ion chelators to macromolecules, both the circulation time and the image contrast are increased. A longer image acquisition time that allows multiples scans, an increase in the paramagnetic ion concentration, and a larger rotational correlation time associated with macromolecules all serve to enhance the signal-to-noise ratio for higher contrast and resolution (Wen et al., 2004; Lee et al., 2005). The rotational correlation time, which is related to the time for rotation of the molecule, greatly contributes to the overall relaxation rate, with greater rotational correlation times improving image contrast (Caravan et al., 1999, Chem. Rev. 99:2293-2352). Several different macromolecular scaffolds have been used in MRI agents. Synthetic polymers have been employed both as linear polymers, most commonly polylysine (Opsahl et al., 1995, Acad. Rad. 2:762-767) and polyethylene glycol (PEG) (Desser et al., 1994, J. Mag. Res. Imaging 4:467-472), and as dendrimers (Kobayashi and Brechbiel, 2005, Ad. Drug Del. Rev. 57:2271-2286; Langereis et al., 2006, NMR in Biomed. 19:133-141). Polyethylene glycol chains have been added to other polymers to modulate the pharmacokinetic properties of the contrast agents since PEG shields the macromolecule and increases retention time (Caravan et al., 1999).

In contrast to synthetic linear polymers that are generally polydisperse, dendrimers are highly branched polymers that are almost monodisperse. The high density of end groups provides many sites for chelator conjugation, which can increase the relaxivity for greater contrast. Furthermore, the rigid structure and shape of dendrimers increases the overall tumbling of the molecule for a larger rotational correlation time (Caravan et al., 1999). Although there have been improvements in syntheses of dendrimers, their preparation still require labor-intensive, multi-step processes. Naturally occurring polymers of sugars and polypeptides, which can be degraded in the body, have been investigated as macromolecular CA backbones. Dextran, which consists of glucose subunits, has been used as a blood pool agent (Sirlin et al., 2004, Acad. Rad. 11:1361; Huber et al., 1998). However, dextran is a polydisperse material, which has limited solubility in some preparations, causing difficulty in the preparation and characterization of the contrast agents.

Proteins such as human or bovine serum albumin (HSA or BSA) (Wang et al., 2004; Caravan et al., 1999), avidin (Langereis et al., 2004, Org. Bio. Chem. 2:1271-1273), and monoclonal antibodies (Shahbazi-Gahrouei et al., 2001, J. Mag. Res. Imaging 14:169-174) have been explored as contrast agents. Human or bovine serum albumin based contrast agents are used as "gold standard" blood pool agents since they are able to distinguish between benign and malignant tumors based on hyperpermeability of tumor vasculature (Caravan et al., 1999; Wang et al., 2004).

Liposomes are other natural macromolecules that can act as contrast agents. They can encapsulate gadolinium chelators in the aqueous compartment of a lipid bilayer coated vesicle, or chelators can be conjugated to the lipids that form the bilayer (Strijkers et al., 2005, Magma 18:186-192; Lanza et al., 2004, Curr. Pharma. Biotech. 5:495-507). However, these can be restricted to diffusion of water with liposomes, limiting proton exchange and therefore, image contrast.

Gadolinium (III) ions are toxic to a biological system on their own, but their strong chelation by an organic molecule prevents the body from the harmful effects of the metal ion. Low-molecular weight contrast agents pose very little safety risk and are widely known to be among the safest drugs that have ever been introduced (Caravan et al., 1999). Their efficient secretion from the body minimizes exposure of the contrast agent and limits the chance of uptake into cells. Furthermore, these low molecular weight contrast agents are secreted unaltered and intact, so the free organic molecule and free metal ions are not circulating in the body. In contrast, there are safety concerns with slow excretion of macromolecular Gd(III) complexes that may result in the build-up of toxic Gd(III) ions (Lu et al., 2003, Mag. Res. Med. 51:27-34). By virtue of their size, macromolecular contrast agents dwell longer in the body and they are not excreted as completely. Metabolism and partial degradation of the macromolecular contrast agents could potentially result in the release of free Gd(III) ions; degradation in low-pH lysosomes can cause the paramagnetic ion to dissociate from the chelator, resulting in free Gd(III). The macromolecular dendrimeric contrast agents have the advantage of extremely narrow molecular weight distribution, but they are not biodegradable (Wen et al., 2004). Additionally, large multivalent molecules are more likely to be antigenic than small molecules, leading to antibodies and potentially anaphylactic shock (Caravan et al., 1999). Serum albumin-based contrast agents particularly pose the threat of an immunogenic response (Wen et al., 2004).

To lower toxicity while maintaining the improved image intensity that comes from a macromolecular scaffold, researchers have designed rapidly biodegradable polymer-based contrast agents. One group has created polydisulfide-based biodegradable macromolecular Gd(III) complexes that can be cleaved through the disulfide groups into smaller complexes that are more readily eliminated from the body though renal filtration (Mohs et al., 2004, Bioconj. Chem. 15:1424-1430; Zong et al., 2005, Meg. Res. Med. 53:835-842; Wang et al., 2004). Another group designed and evaluated poly(L-glutamic acid)-based (PGA-based) contrast agents, since PGA is readily degraded by lysosomal enzymes to L-glutamic acid, a nontoxic natural compound (Wen et al., 2004).

Regenerating tissues is a challenging, important area in medicine that is a potential therapy for a vast number of diverse diseases. Because of the three-dimensional and non-invasive advantages as well as the ability to provide cellular resolution, MRI is an ideal imaging tool to track the fate of tissue engineering scaffolds and cells, cellular remodeling, angiogenesis, and other important parameters. Researchers have performed MRI with Gd-DTPA contrast agents to study various aspects of tissue engineering in bladders (Chang et al., 2005, J. Mag. Res. Imaging 21:415-423), meniscal cartilage (Neves et al., 2006, Tissue Eng. 12:53-62), and the heart (Barbash et al., 2004, Heart 90:87-91). The scaffold is a key part of tissue engineering, providing physical support and chemical signals for cellular growth. Mechanical properties, degradation rate, porosity, chemical composition, incorporated bioactive factors and other scaffold variables together determine the success of growing cells. Thus, there has been significant research using MRI to study various implantable biomaterials that act as scaffolds (Barbash et al., 2004; Neves et al., 2006; Stroman et al., 1999, Mag. Res. Med. 42:210-214; Guidoin et al., 2004, Art. Cells, Blood Subs., 1 mm. Biotech. 32:105-127; Pihlajamaki et al., 1997, Biomat. 18:1311-1315). Additionally, peptide amphiphile contrast agent molecules have been created that attach contrast agents to biomaterials that act as a tissue engineering scaffold, enabling imaging of the scaffold (Bull et al., 2005, Bioconj. Chem. 16:1343-1348; Bull et al., 2005. Nano Lett. 5:1-4).

In addition to increasing contrast, there has been work done on targeting MRI agents to particular tissues. Generally, MRI contrast agents are injected systemically and passively, and non-specifically enhance the MRI signal. There are blood pool agents that highlight the vasculature in normal and cancerous tissues. On the other hand, targeted contrast agents can be modified so that they localize to a specific tissue or cell type. A variety of ligands with high affinity and specificity to their receptor have been coupled to contrast agents for active targeting. Monoclonal antibodies or their fragments (Morawski et al., 2005, Curr. Opin. Biotech. 16:89-92), peptides, peptidomimetics, and aptamers are among the ligands that can be coupled covalently or non-covalently (Lanza et al., 2004). Receptors HER-21/neu, which are expressed on the surface of malignant breast cancer cells, were imaged using a biotinylated herceptin antibody and avidin-conjugated contrast agent (Artemov et al., 2004). The RGD epitope, which mimics the fibrinogen binding site to the $\alpha_v\beta_3$ integrin, has been incorporated into MRI contrast agents to image angiogenesis (Mulder et al., 2005, FASEB J. 19:2008-2010). In addition to targeting extracellular components, there is great interest in designing contrast agents that can cross the cellular membrane to allow intracellular imaging. There are known short peptides (less than 30 residues) with translocation properties, including the tat peptide from the HIV tat protein, polyarginine, and penetratrin (Lanza et al., 2004). Investigations with peptides showed that the role of positive charges is critical in effectively crossing cell membranes. Mitchell et al., 2000, J. Peptide Res. 56:318-325 showed that polyarginine containing six or more amino acids crosses cell membranes far more effectively than histidine, ornithine, or lysine polymers of equal length or longer. Both the tat protein (Wunderbaldinger et al., 2002, Bioconj. Chem. 13:264-268) and polyaxginine (Allen and Meade, 2003, J. Biol. Inorg. Chem. 8:746-750; Allen et al., 2004, Chem. Biol. 11:301-307) have been covalently attached to contrast agent platforms and shown to permeate cell membranes and improve intracellular MRI contrast. Additionally, steroid hormones have been conjugated to contrast agents to image intracellular signaling pathways (Lee et al., 2005). However, the aforementioned conjugated contrast agents are time consuming and inefficient to produce, as well as being polydisperse for limited gadolinium chelating.

As such, what are needed are compositions and methods for use in magnetic resonance imaging that not only increase imaging sensitivity and contrast, but also can be used to increase the utility of MRI in research and for diagnostics and therapeutic uses for patient health care.

SUMMARY OF THE INVENTION

The present application provides for compositions and methods of creating multivalent contrast agents that find use in magnetic resonance imaging (MRI). In particular, contrast agents are described that comprise monodisperse, protein polymer backbones capable of chelating multiple paramagnetic ions resulting in high relaxivity for use in enhancing MRI signal intensity.

Artificial protein polymers generated through cloning and recombinant protein expression were naturally produced for use as the macromolecular backbone of a CA. A gene was designed and created for producing a protein polymer, the gene was transformed into $E.\ coli$ bacteria using techniques known in the art, and the bacteria were induced to produce the protein. The protein polymers are designed to obtain specific properties, including solubility, reactivity, and the ability to be incorporated into hydrogels for tissue engineering. In contrast to natural biological (e.g., dextran) and synthetic polymers, the chemical makeup and length of these protein polymers are controlled. Long, monodisperse proteins with evenly spaced reactive sites, creating a construct that is an ideal backbone for a defined multivalent CA were thereby created.

In some embodiments, the genetically engineered protein polymer backbone of these multivalent CAs comprises a repetitive amino acid monomer unit. For example, in one embodiment, the protein contains thirty repeats of the monomer, GKAGTGSA (SEQ ID NO:1), providing thirty evenly spaced reactive lysines that are available for modification. However, the invention is not limited to the sequence of the repeated monomer, and other sequences and lengths (e.g., 2 repeats, 3 repeats, 4 repeats, 5 repeats, 6 repeats, 7 repeats, 8 repeats, 9 repeats, 10 repeats, 15 repeats, 20 repeats, 30 repeats, 40 repeats, 50 repeats, 60 repeats, 90 repeats, 120 repeats, etc.) are contemplated as long as the protein monomers maintain monodisperse reactive sites for metal chelators. For example, sequences are contemplated that contain targeting domains to tumors or cells and organs are envisioned. Further, sequences are contemplated that are water soluble, plus sequences are contemplated that are organo-soluble. An exemplary 21,750 dalton protein polymer as described herein was designed to be water soluble (e.g., for in vivo applications) and to have a random coil configuration.

As such, the backbone of multivalent MRI contrast agents as described herein is derived from $E.\ coli$ expression of monodisperse artificial protein polymers. Gd(III) chelators are chemically conjugated to the backbone to create contrast agents that display high relaxivity in solution and as a gel. It is contemplated that covalent incorporation of these protein polymer contrast agents into a gel allows the potential use of these CAs in imaging and tissue engineering scaffolds.

In some embodiments, the present invention provides a contrast agent comprising a gadolinium-chelated monodisperse protein polymer, wherein said protein polymer is produced in bacteria. In some embodiments, the gadolinium is gadolinium(III). In some embodiments, the monodisperse protein polymer comprises evenly spaced lysine resides, for example, as found in a monodisperse protein polymer comprising SEQ ID NO: 1. In some embodiments, the protein polymer comprises at least 30 repeats of a peptide, for example SEQ ID NO: 1, whereas in other embodiments the protein polymer comprises at least 60, at least 90, at least 120 repeats of a peptide, for example SEQ ID NO: 1. In some embodiments, the bacteria used to produce the protein polymer is an $E.\ coli$ strain. In some embodiments, the present invention provides gadolinium-chelated, monodisperse protein polymers that are biodegradable, non-toxic, and/or cell-permeant.

In some embodiments, the present invention provides a method of increasing contrast in magnetic resonance imaging, comprising, applying a contrast agent such as gadolinium chelated monodisperse protein polymer to a subject and performing MRI on that subject after applying the gadolinium chelated monodisperse protein polymer. In some embodiments, the gadolinium chelated monodisperse protein polymer is applied to a mammal, preferentially to a human. In some embodiments, the gadolinium chelated monodisperse protein polymer that is applied to a subject comprises evenly spaced lysine residues, such as those found in SEQ ID NO: 1, wherein said monodisperse protein polymer preferentially comprises at least 30 repeats the SEQ ID NO: 1. In some embodiments, the gadolinium chelated monodisperse protein polymer applied to a subject is biodegradable, non-toxic, and/or cell-permeant.

DEFINITIONS

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, where "amino acid sequence" is recited herein to refer to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include post-translational modifications of the deduced amino acid sequences, such as amino acid deletions, additions, and modifications such as glycolsylations and addition of lipid moieties.

The term "gene" refers to a nucleic acid (e.g., DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements, as described below.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

DETAILED DESCRIPTION OF THE INVENTION

The present invention provides a novel class of biosynthetically produced protein polymers that find utility as scaffolds for macromolecular contrast agents. Proteins can be obtained in high yield through *E. coli* (or another host organisms') inherent synthetic machinery and protein production is easily scaled up to provide large amounts of the protein polymers. The repetitive proteins as described herein contain evenly spaced lysines, enabling conjugation to gadolinium (Gd) ions chelated by a small organic molecule. A chemical coupling scheme is utilized to produce protein polymer-based contrast agents that exhibit extremely high relaxivity, both per Gd ion and per molecule. In addition to providing higher contrast MRI, the monodispersity of these protein-based CAs find utility for in vivo applications.

Protein polymers possess many advantages over traditional polymers, making them highly desirable for use as biomaterials. The protein polymer as described herein comprises the 20 natural amino acids that are already in the body. As such the construct is contemplated to be non-immunogenic. In contrast to traditional polymers, the protein polymers in embodiments herein are entirely monodisperse, so the number of repeated units is the same throughout the entire mass of protein. In addition to controlling the number of repeat units, the sequence of the protein is designed such that the number of reactive side chains is manipulated. It is contemplated that these aforementioned properties allows the creation of defined protein polymers with customizable length, reactivity, architecture, and solubility. Additionally, it is contemplated that additional components (e.g., fluorophores, targeting moieties, cellular transporters) are attachable to these customizable protein backbones. Toxicity is a concern in any substance that is intended for use in the body and macromolecular contrast agents may present a risk of exposure to free gadolinium. However, it is contemplated that the protein polymer scaffolds as described herein are biodegradable through normal protease activity into small, excretable components, thereby alleviating safety concerns.

In some embodiments, the protein is designed to be water-soluble, histocompatible, and contain a random coil conformation. It is preferably a long repetitive protein with a monomer sequence of eight amino acids that are not charged at neutral pH except for a lysine residue, which is positively charged. Exemplary sequence design is based on a protein that has the amino acid sequence of GKGSAQA (glycine-lysine-glycine-serine-alanine-glutamine-alanine; and that expresses well in E. coli (Won and Barron, 2002, Macromol. 35:8281-8287). Glutamine deamidation occurs with this sequence, so the preliminary sequence cloned is re-designed without a glutamine and the resulting monomer sequence is GKAGTGSA (glycine-lysine-alanine-glycine-threonine-glycine-serine-alanine; SEQ ID NO:1). The spacing allows sufficient room for the Gd chelator so that there will not be steric repulsion inhibiting conjugation at neighboring reactive sites by maintaining a high density of reactive lysines. The eight amino acid monomer is repeated, for example, thirty times in the protein polymer, creating a backbone with 30 reactive sites. Additional exemplary monomer repeats of 60 and 120 have been synthesized thereby creating backbones with increased numbers of reactive sites. However, the present invention is not limited by the length and therefore the number of reactive sites. Moreover, the protein polymers need not comprise evenly spaced lysines in every part of the sequence along the backbone. For example, protein polymers with "block-like" sequences, having different lysine spacings along the backbone, can also be created by additional controlled cloning procedures, as known to those skilled in the art.

The cloning method is a multi-step process that was developed by Won and Barron, 2002. The desired target protein is translated into the corresponding DNA sequence. Because of the degeneracy of the genetic code, multiple oligonucleotide sequences can correspond to an amino acid and the specific nucleotides are designed to take into account the transcription and translation preferences of E. coli. The oligonucleotide sequence is amplified by polymerase chain reaction (PCR) to generate a large quantity of the blunt-ended gene. The DNA is digested with the enzyme Eamll04 I to create adhesive ends and either ligated into a plasmid or multiple units are allowed to self-ligate to form a multimer. In order to ligate two genes together in a controlled fashion, the DNA was digested with different enzymes such that they cannot self-ligate. The enzymes Eamll04 I and Sap I are used to digest the two different genes. The nucleotide recognition sequences of these restriction enzymes vary by one nucleotide, such that Eamll04 I can cleave a Sap I site, but the reverse is not true. Calf intestinal alkaline phosphatase (CIAP) is employed to dephosphorylate the Eaml 104 I digested DNA, yielding only one ligation scenario in the subsequent ligation of the two DNA populations. After ligation of the two DNA populations, the combined ligated gene is further ligated into the pET19 expression plasmid and transformed into BLRDE E. coli cells following standard protocols.

To express the recombinant protein, the transformed cells were grown in Terrific Broth media with 1 mM ampicillin and 1 mM tetracycline and bacterial cells containing the plasmid were selected for via antibiotic resistance. The cells are grown to an optical density at 600 nm of 0.6 to 0.8 and induced to express the recombinant protein with 1 mM of isopropylthiogalactoside (IPTG). Following expression, the cells were lysed and the protein polymers were purified through nickel affinity chromatography using imidazole competitive elution. The pE19 plasmid contains a sequence for a decahistidine tag (10×HIS tag) that is expressed along with the recombinant protein. The histidine tag contains a lysine residue, so it provides an extra reactive site for the Gd chelators. The ten histidine amino acid residues bind to nickel resin such that the desired recombinant protein can be separated from all other proteins present in the cell lysate. The expressed proteins were confirmed through matrix assisted laser desorption ionization-time of flight mass spectrometry (MALDI-TOF MS) and protein sequencing. It is possible to cleave off the histidine tag using cyanogen bromide in formic acid, but this was not deemed necessary.

A derivatized DO3A gadolinium chelator was utilized for complexing with the protein polymer. The three shorter arms were used to chelate the Gd ion while the carboxyl group on the 5-carbon arm to form a covalent bond with the primary amine on the lysine residues in the protein backbone. The DO3A gadolinium molecule was synthesized with protected tert-butyl groups on the three shorter arms. Additionally, the tert-butyl groups were cleaved off of the molecule and the DO3A derivative was incubated with gadolinium salt to produce the deprotected chelator with the Gd ion.

Since the protein polymers are water-soluble and the chelator with the Gd ion is also water soluble, chemical conjugation of the Gd chelators to the backbone was performed using EDC and Sulfo-NHS in a filtered 0.1 M MES, 0.5 M NaCl buffer. The protein was dissolved at 1 mg/ml in the MES buffer and the final reaction solution was adjusted to pH 7.0. The reaction proceeded for 24 hours and was dialyzed for 3 days and lyophilized. The dried conjugate was resuspended in water and filtered with a 0.45 um polytetrafluoroethylene (PTFE) syringe filter and re-lyophilized. As determined through MALDI, as many as 13 Gd chelators was conjugated per backbone (30 mer), a 42% site coverage, as indicated by the molecular weight shift from 21,750 Da before the conjugation reaction to 29,200 Da afterwards.

Figure 5:
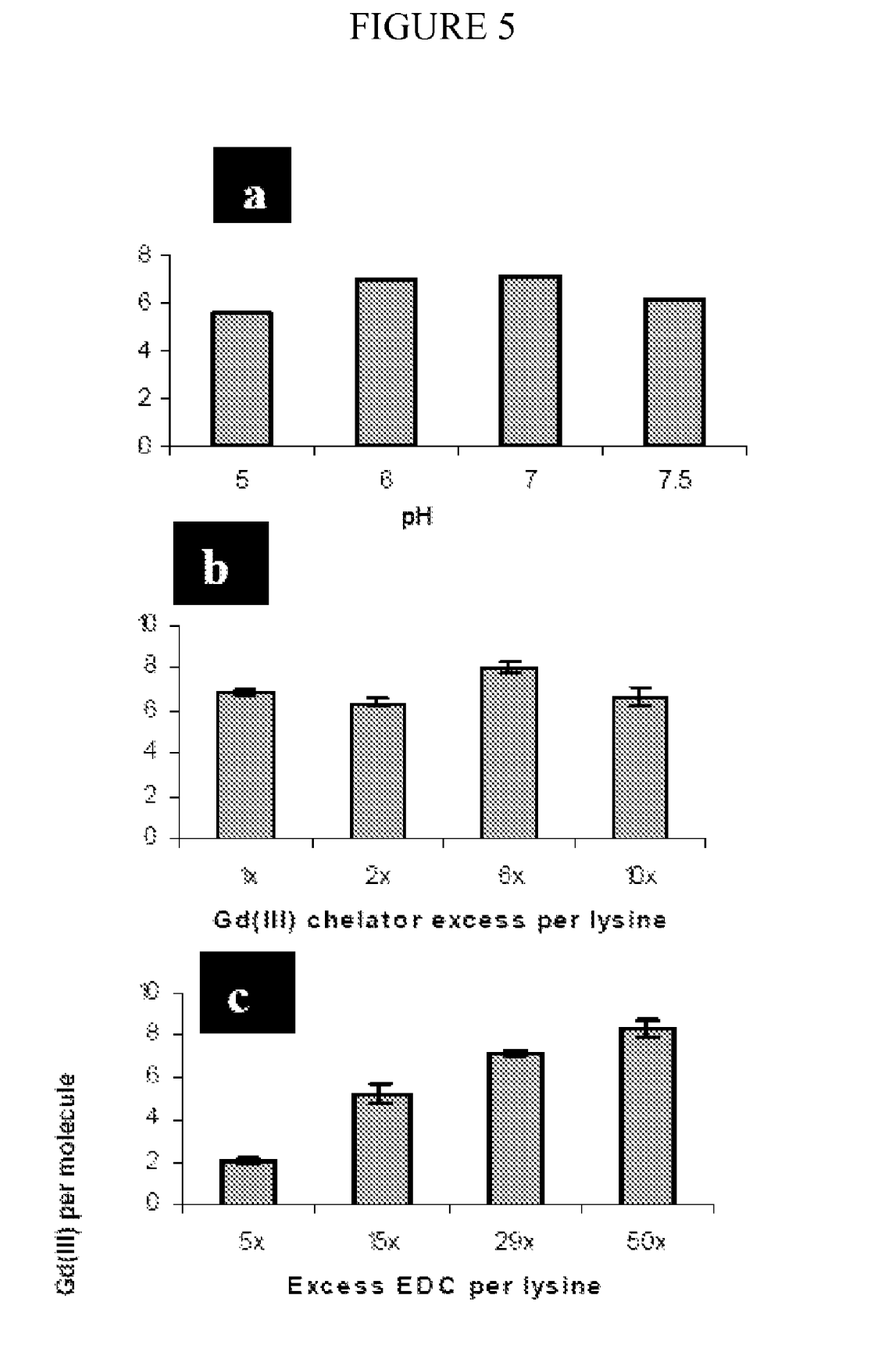
FIG. 5 demonstrates the effect of a) pH, b) Gd(III) chelator excess and c) EDC excess, on conjugation efficiency.

In developing embodiments of the present invention, experiments designed to effect improvements in the conjugation efficiency between the protein polymer and the chelator were undertaken. Parameters such as pH, excess chelator in a reaction, and excess of EDC (1-ethyl-3-[3-dimethylaminopropyl]carbodiimide hydrochloride) in the buffer were examined. It was determined that the optimal reaction pH was between pH 6-7 (FIG. 5a), excess chelator (Gd(III)) at six times molar excess per lysine residue (FIG. 5b) and that higher EDC excess per lysine residue (FIG. 5c) all resulted in improvements in conjugation efficiency.

Inductively coupled plasma mass spectrometry (ICP-MS) measurements were performed to obtain relaxivity per Gd. Relaxivity of Gd up to 15.6 mM$^{-1}$ s$^{-1}$ was obtained. Using the MALDI measurements to calculate the number of Gd chelators per molecule, we have obtained a relaxivity of up to 229.1 mM$^{-1}$ s$^{-1}$ per molecule. The relaxivity per Gd and per molecule of these protein polymer contrast agents is higher than literature values, excluding viral capsid contrast agents. However, these contrast agents based on viral protein nanoparticles are not as customizable. In contrast, protein polymers are easily produced though and scaleable to produce large quantities. The initial contrast agents produced demonstrated that these protein polymer-based CAs have extremely high relaxivities, showing the potential to be valuable in various MRI applications.

Figure 6:
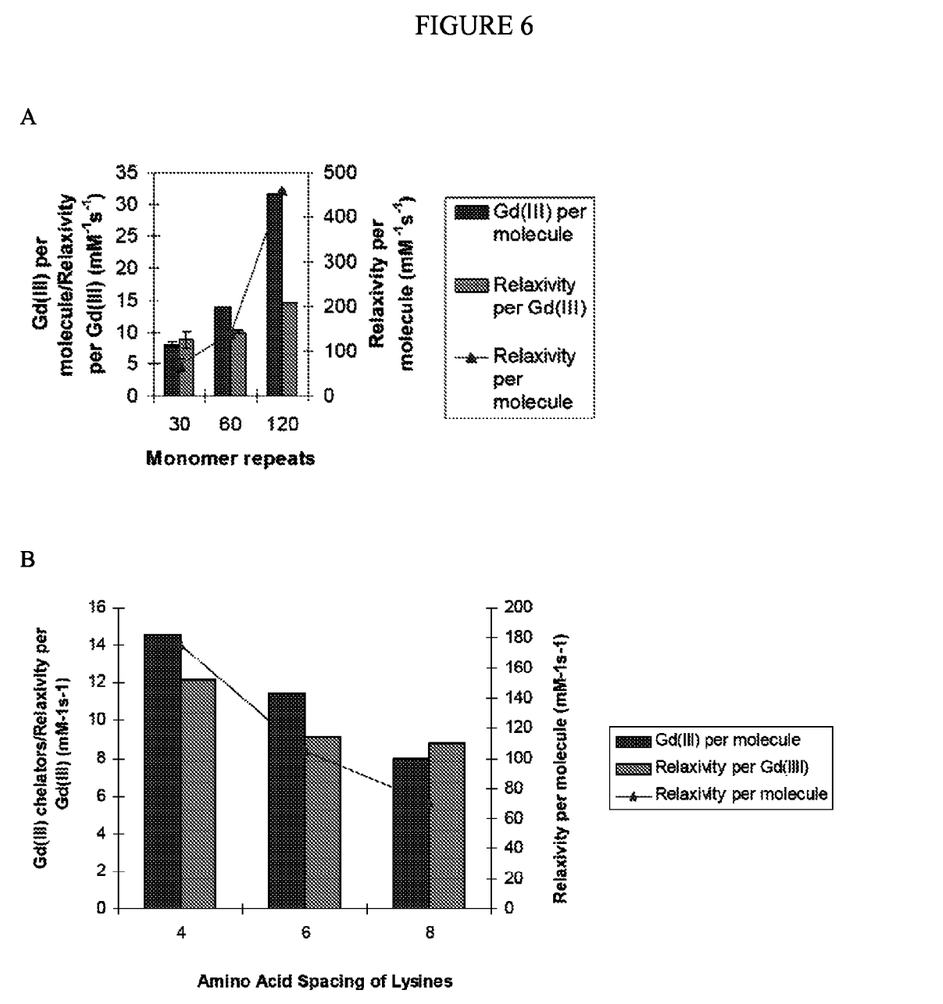
FIG. 6 demonstrates the dependence of relaxivity on a) protein polymer length, where each exemplary monomer repeat is GKAGTGSA and b) lysine spacing.

In a parallel strategy to improving conjugation efficiency as described above, experiments were performed in developing embodiments of the present invention to improve the relaxivity per chelator. An important variable in determining relaxivity is $\tau_R$, the rotational correlation time (i.e., the molecule's rate of tumbling in solution). Larger $\tau_R$, which indicates slower rotation and generally arises from higher molecular weight, increases relaxivity. Thus, two protein polymers with longer lengths, composed of 60 and 120 repeats (40.6 kDa and 78.4 kDa, respectively), were explored in comparison to the 30-repeat, 21.7-kDa protein polymer. The proteins were cloned, expressed and used in conjugation reactions under the same reaction conditions (e.g., pH 6.5, six times Gd(III) chelator excess per lysine residue). As can be seen in FIG. 6A, and synopsed in Table 1, as molecular weight of the protein chain increases, the relaxivivty per Gd(III) increases from 8.8 to 14.0 mM$^{-1}$ s$^{-1}$. Moreover, the relaxivity per molecule increased from 70.5 mM$^{-1}$ s$^{-1}$ for 30 repeats to 443.5 mM$^{-1}$ s$^{-1}$ for 120 repeats due to the additional sites available for derivitazation with chelators. As such, it is contemplated that as backbone size increases, so does relaxivity.

TABLE 1

| | Monomer Repeats | | |
|---|---|---|---|
| | 30 | 60 | 120 |
| Gd(III) per molecule | 8 | 13.9 | 31.6 |
| Relaxivity per Gd(III) (mM$^{-1}$s$^{-1}$) | 8.8 | 10.0 | 14.6 |
| Relaxivity per molecule (mM$^{-1}$s$^{-1}$) | 70.5 | 138.9 | 461.4 |
| Conjugation Efficiency | 0.27 | 0.23 | 0.26 |

The present invention is not limited to the size of the protein backbone, and indeed longer polymeric proteins comprising, but not limited to, at least 150 repeated sequences, 170 repeats, 200 repeats, etc. are comtemplated. Further, polymeric proteins of less than 30 repeated sequences are contemplated such as, but not limited to 5 repeats, 10 repeats, 20 repeats, etc.

Alternate lysine spacings were also explored in addition to longer lengths of protein polymers. Rotation of the chelators is another important factor in determining relaxivity, where, for example, less rotation provides higher relaxivity. It was contemplated in developing embodiments of the present invention that a higher density of reactive sites could decrease chelator rotation, thereby increasing relaxivty per Gd(III). Proteins with lysines every 6 amino acids with the monomer repeat GKGTGA (SEQ ID NO: 8), and proteins with lysines every 4 amino acids with the monomer repeat GKGSGKGA (SEQ ID NO: 9) were cloned and expressed in lengths of 40 repeats (21.7 kDa) and 30 repeats (22.1 kDa), respectively. The molecular weights of these protein polymers are close to that of the original protein with lysines every 8 amino acids and 30 repeats. The effect of the lysine spacing can be analyzed without the complicating factor of variation in molecular weight. As shown in FIG. 6B and Table 2, CAs with lysines spaced every 6 and 8 amino acids apart have similar relaxivities. However, CAs with lysines spaced every 4 amino acids apart had higher relaxivity per molecule. The present invention is not limited to a particular mechanism. Indeed, an understanding of the mechanism is not necessary to practice the present invention. Nonetheless, it is contemplated that this effect could be due to increased steric interactions that cause more rigidity and thus a higher relaxivity.

TABLE 2

| | (BB3)10 average | (BB2)10 average | (BB4)10 average |
|---|---|---|---|
| Lysine Spacing | 4 | 6 | 8 |
| Gd(III) per molecule | 14.55398 | 11.5 | 8 |
| Lysines per protein | 61 | 41 | 31 |
| Relaxivity per Gd(III) | 12.13333 | 9.1 | 8.8 |
| Relaxivity per molecule | 175.3797 | 104.7 | 70.5 |
| Conjugation efficiency | 0.24 | 0.280488 | 0.27 |

Figure 3:
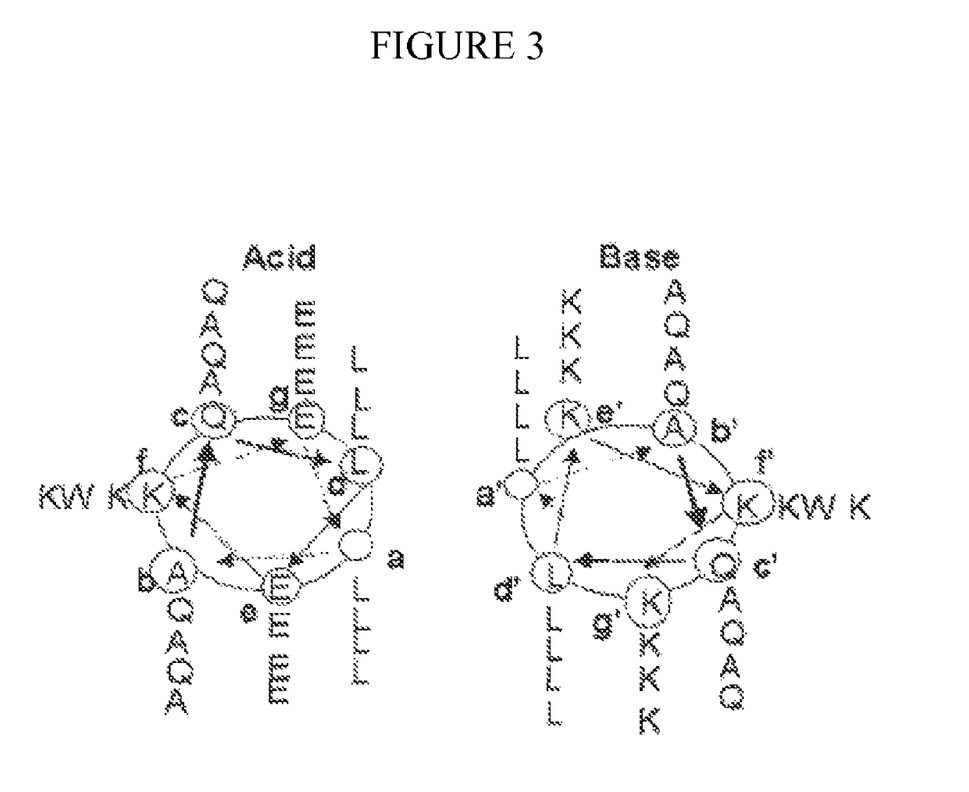
FIG. 3 shows α and β coiled coil helical wheels.

Increasing the concentration of Gd ions by complexing self-assembling proteins with random coil protein scaffolds is also contemplated. The proteins are designed to be water-soluble, biocompatible protein-based block copolymers with defined sequences that include both the random coil protein domain and an amphipathic helical domain that forms "coiled-coil" quaternary structure. Two separate coiled-coil protein domains, one with positively charged residues (the "acid sequence") and one with negatively charged residues (the "base sequence"), self-assemble into a heterotetramer with two acid and two base units. In this block copolymer design, the section of the protein backbone that is connected to the random coil forms an α-helix that can self-assemble with other α-helices to form a "coiled-coil". Typically, the amino acid sequences of coiled-coils consist of a heptad repeat of seven amino acid residues denoted a to g, as shown in the helical wheel in FIG. 3. The residues at the a and d positions are typically hydrophobic, while the e and g positions are typically charged. The interactions between the a, d, e, and g residues on each helix physically crosslink the proteins. A block copolymer of each of two α-helix proteins with the random-coil protein is formed. One α-helix, designated the acid, contains the sequence, AQLEKELQALE-KELAQLEWZLQALEKELAQ (SEQ ID NO:2). The other sequence, the base, contains the amino acid sequence AQLKKKLQALKKKLAQLKWKLQALKKKLAQ (SEQ ID NO:3). When the acid and base α-helices are together in solution, they self-assemble into a heterotetramer with two acid and two base units, predominantly in an anti-parallel orientation (Lumb and Kim, 1995, Biochem. 34:8642-8648). When the block copolymer proteins are mixed together, it is contemplated that they will self-assemble to form a complex with the four random-coil chains emanating out from the central self-assembled coiled-coil region. Although the complex will be physically crosslinked via non-covalent intermolecular interactions of the coiled coil domains, additional stability is accomplished by covalently linking the chains together. Also, since there are lysine residues in the coiled coil, it is contemplated that these will react with the chelator, destabilizing the heterotetramer. The enzyme, tissue transglutaminase (tTG), which catalyzes a calcium-dependent acyl transfer between glutamine and lysine, will be used to execute the crosslinking (Hu and Messersmith, 2003). Although the lysine environment is less particular, tTG prefers specific amino acids surrounding the glutamine and lysines that participate in the acyl transfer. Hu and Messersmith, 2003, found optimized substrates QQQLG for glutamine and FKG for lysine. As such, these peptide substrate sequences will be included between the random-coil and coiled-coil sections, so that tTG can be used to covalently crosslink the four protein chains into one stable complex after they have self-assembled.

In developing embodiments of the present invention, the peptide sequence GQQQLG (SEQ ID NO: 7) was created so that the reaction substrates could be reversed; for example a chelator with a terminal amine is attached to a protein polymer with a glutamine substrate in the backbone via the tTG. As such, a protein polymer comprising 12 repeats of GQQQLG was conjugated with a DO3A chelator comprising a six-carbon arm and a terminal amine. Results demonstrated (MALDI) that approximately 2.5±0.6 chelators were attached per protein molecule, thereby providing an alternative strategy for creating monomeric protein/chelator contrast agents.

Conversely, transglutaminase can also be used to perform the conjugation between lysines in the protein backbone and the glutamine substrate attached to the chelator. For example, the glutamine peptide substrate, QQQLG, can be synthesized on a peptide synthesizer with protected Qs. The peptide can be conjugated to the tert-butyl protected DO3A derivative with volatile organic solvents, such as NMP, using, for example, a peptide-coupling agent such as PyBroP or HATU in DIEA. The tert-butyl groups and protecting groups are then removed using trifluoroacetic acid (TFA). The resulting conjugate complex is incubated with gadolinium salt. The chelator and protein are enzymatically crosslinked through the glutamine substrate on the chelator and the lysine substrate on the backbone with TG, using similar conditions used in Hu and Messersmith, 2005, Ortho. Cranio. Res. 8:145-149 (incorporated herein by reference in its entirety). It is contemplated that this enzymatic crosslinking provides an effective way to achieve high conjugation site coverage.

In order to both increase solubility of the protein backbone in organic solvents and to include a better enzymatic transglutaminase substrate for conjugation to chelators, a phenylalanine amino acid (F) will be added to the random coil backbone, resulting in GFKAGTGSA (SEQ ID NO: 4). It is contemplated that this protein structure will not form a particular secondary structure, behaving as a random coil in an aqueous solution. As indicated by the monomer sequence, the lysines are spaced every nine amino acids, which is still an optimal interval for a high concentration of Gd chelators, but still allowing enough room to prevent steric hindrance. However, it was determined that the protein polymer GFKAGTGSA was not soluble in organics and is only soluble in water at high pH. It is contemplated that proteins including various amounts of leucines, a hydrophobic residue that is high on the hydropathy scale, provides novel protein polymers useful in the present invention that are both water and organo-soluble.

Without the phenylalanine residue, the random coil protein is not soluble in organic solvents and the copolymer protein is likely also not soluble in organic solvents. However, a protein soluble in organic solvents would allow coupling in N-methyl-pyrrolidone (NMP) using a peptide coupling agent such as Bromo-tris-pyrrolidinophosphoniumhexafluorophosphate (PyBroP) or 2-(IH-7-Azabenzotriazol-1-yl)-1,1,3,3-tetramethyluroniumhexafluorophosphate Methanaminium (HATU) in diisopropylethylamine (DIEA). Two equivalents of the chelator and at least 2:1 equivalents of the peptide-coupling agent will be used for each lysine site. Chemical conjugations in organic solvents are much more efficient than in aqueous solutions, so a higher efficiency of Gd-protein coupling will occur.

Figure 2:
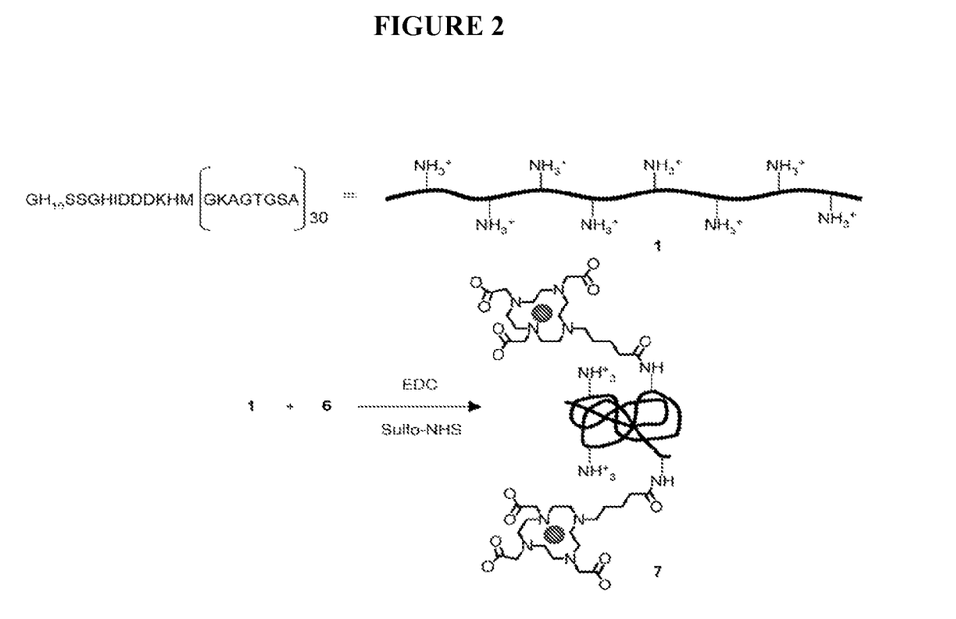
FIG. 2 shows an exemplary conjugation of Gd(III) chelator to the protein polymer backbone by standard coupling conditions. This scenario provides ~10 chelators per protein molecule.
Figure 4:
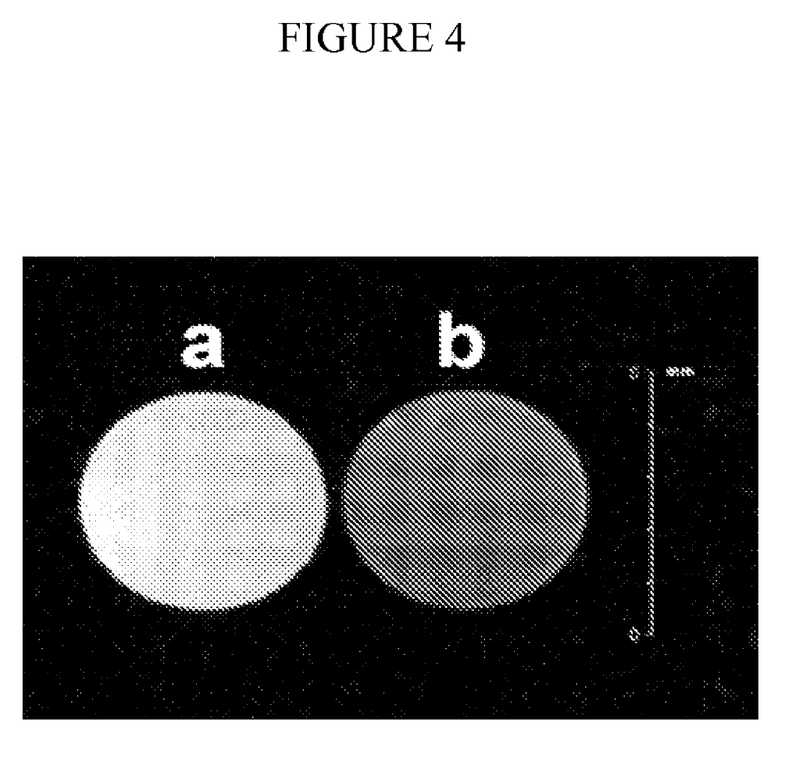
FIG. 4 shows MR images taken at 600 MHz, a) is the gel doped with protein polymer CA with a Gd(III) concentration of 0.8 mmol and b) is the control gel without CA.

These customizable protein polymers also find use in hydrogels for tissue engineering by conjugating bioactive factors and peptide substrates that enable enzymatic crosslinking. Thus, the protein polymer-based materials are combined to enable MRI of the implanted tissue-engineering scaffold over the lifetime of the animal. The protein polymer with Gd chelators is added to the hydrogel material at appropriate concentrations to achieve sufficient image intensity. Indeed, as seen in FIG. 4, contrast enhancement utilizing protein polymer conjugates with Gd(III) as described herein is demonstrated when the contrast agents were crosslinked into a 5.8% (w/v) protein-based hydrogel in aqueous solution with 45 µl of 25% glutaraldehyde. A gel doped with protein polymer CA (FIG. 2, #7) with a Gd(III) concentration of 0.8 mmol is significantly brighter that a gel without CA. One advantage of the protein polymer based CAs is that at least 50% of the primary amines on the backbone remain underivatized and are available for covalent cross-linking to the hydrogel, as well as assisting in water solubility. Thus, once crosslinked to other proteins within a hydrogel, the multivalent CAs can only be removed from the hydrogel as a result of hydrolysis of the scaffold and not as a result of diffusion. FIG. 4 further demonstrates that the hydrogel incorporating (7) is homogeneous. In some embodiments, such a hydrogel is implanted in vivo in a subject for therapeutic purposes, such as drug delivery, and tracked over time by, for example, MRI.

Incorporation of cellular transporters, the HIV tat peptide and polyarginine, into CAs to enable intracellular MRI is further contemplated. Both the tat peptide, GRKKRRQRRR (SEQ ID NO:5) and the polyarginine (10-14 monomers) peptide are short enough that they can be efficiently synthesized on a peptide synthesizer. Both peptides are conjugated to the protein polymer backbone through conjugation methods as previously described or known in the art. Alternatively, the polyarginine peptide is added onto the protein backbone through controlled cloning and recombinant protein expression as described herein.

Figure 7:
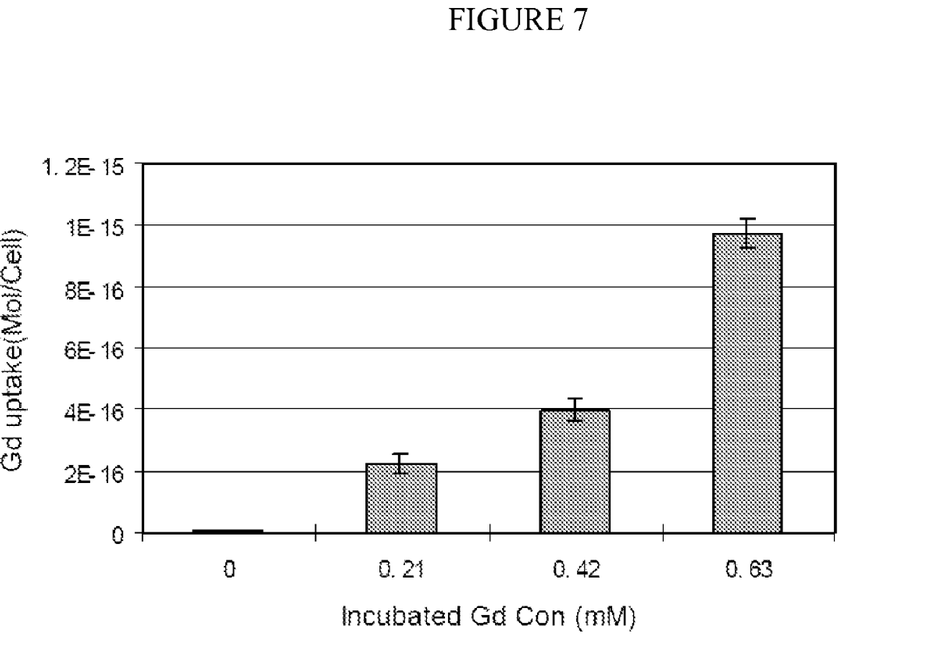
FIG. 7 demonstrates cell uptake after a 5 hour incubation with CA.
Figure 8:
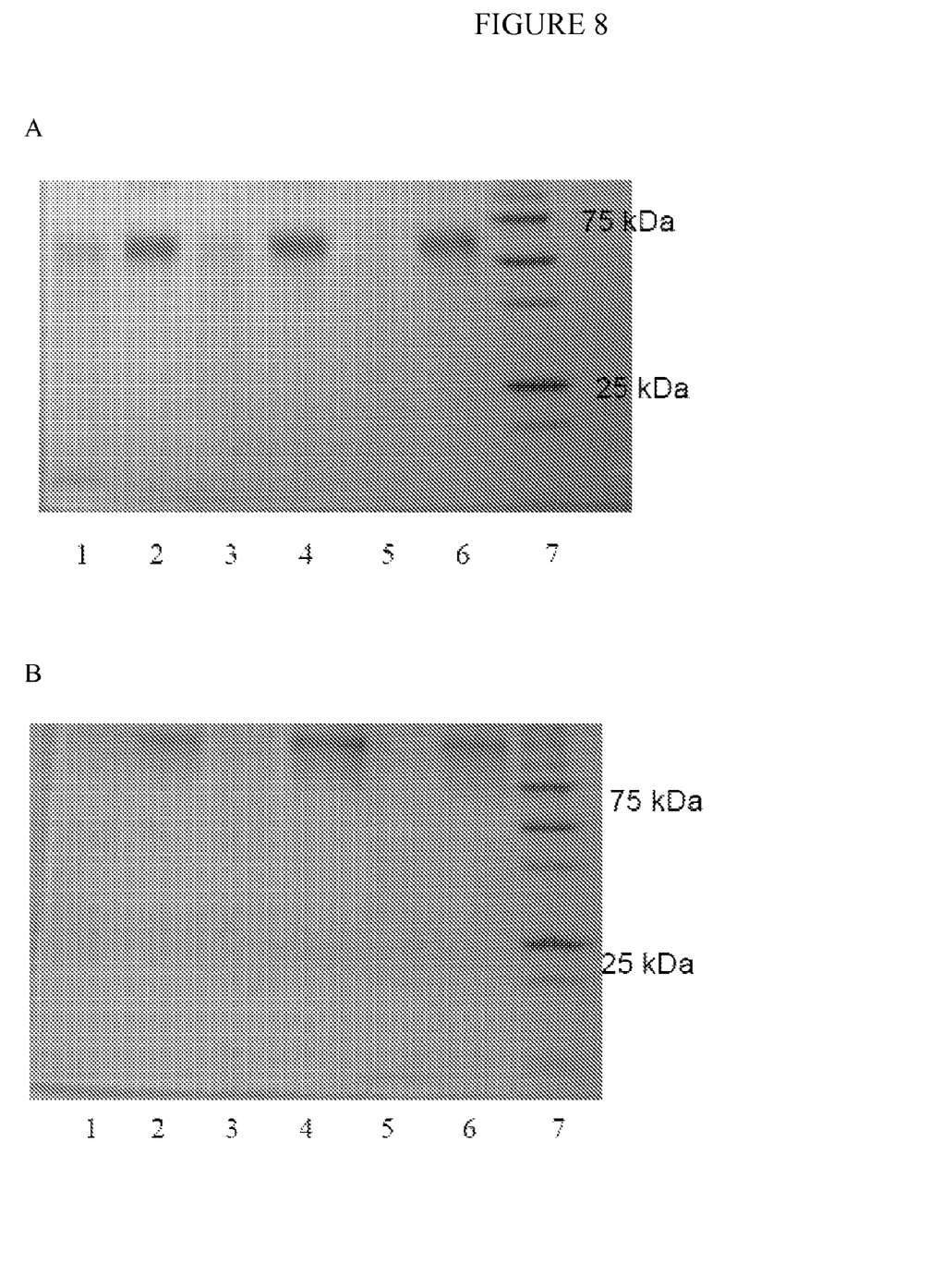
FIG. 8 demonstrates plasmin degradation of a) 60 repeats and b) 120 repeats of GKAGTGSA contrast agent. Lane 1: 3 hours; Lane 2: 3 hours no enzyme; Lane 3: 6 hours; Lane 4: 6 hours no enzyme; Lane 5: 24 hours; Lane 6: 24 hours no enzyme; Lane 7: marker.

If these contrast agents are able to permeate cells, they find use to track cells in vivo. As such, experiments were undertaken to demonstrate cellular uptake of the compositions of the present invention. MIN6 cells were incubated for 5 hours with several concentrations of CAs of the present invention. After the incubation time, cells were counted and submitted to ICP-MS to determine Gd(III) concentration. It was determined that increased CA concentration led to, for example, increased uptake of CAs increased (FIG. 7). Toxicity studies were undertaken to determine if the cellular uptake was toxic to the cells. The Guava Viacount Assay™ was performed using MIN6 cells incubated with exemplary CAs with 30 repeats of GKAGTGSA. Results demonstrated cell viability of approximately 97% after 5 hours incubation in the presence of CAs comprising up to 0.63 mM of Gd(III). As such, the exemplary CAs were virtually non-toxic. Further, degradation studies were performed to determine if the macromolecular CAs of the present invention would degrade in a subject, thereby avoiding safety concerns for potential prolonged circulation of the CAs in a subject. FIG. 8 demonstrates that, when the CAs are incubated with plasmin, a protease that cleaves lysine residues, the CAs are biodegradable. As such, CAs of the present invention are cell-permeant, non-toxic, and biodegradable thereby providing tools for in vivo imaging and therapeutic applications (e.g., drug delivery).

In one embodiment, the present invention provides multivalent, protein polymer-based scaffolds as monodisperse contrast agents for enhancing MRI intensity. In some embodiments, the protein polymers comprise random coil protein structures derivatized with multiple Gd chelators. In some embodiments, the concentration of Gd chelators is increased by enzymatic conjugation to self-assembled coiled-coil proteins. In one embodiment, genes that encode the proteins for the protein polymer scaffolds are produced by genetic engineering and expression in a bacterial system, for example *E. coli*. In some embodiments, the sequence for the encoded protein is GKAGTGSA (SEQ ID NO: 1). However, a skilled artisan will understand that a variety of sequences may be generated using the guidance provided herein, and multiple sequences are applicable as long as free amines for conjugation are maintained. In some embodiments, the protein polymers further comprise the attachment of additional components such as, for example, fluorophores, cellular transport signals, and targeting molecules. For example, in some embodiments, the protein polymers comprise a targeting domain for in vivo use. For example, the tumor target signals and organ or tissue targeting signals can be incorporated in the protein polymer. In some embodiments, the lysines present in the protein are located at least eight amino acids apart to provide reactive primary amines at specific locations, such that steric hindrance is avoided upon attachment of Gd chelators. In some embodiments, the protein polymers are water soluble, while in some embodiments the protein polymers are organosoluble.

In one embodiment, the contrast agents as described herein offer increased intensity for MRI. In some embodiments, the contrast agents are biodegradable. In one embodiment, the contrast agents are monodisperse and able to be characterized. In some embodiments, the contrast agents are used for in vivo applications. In some embodiments, the contrast agents find utility not only as experimental tools, but also in clinical diagnosis. For example, the contrast agents as described herein can target healthy or diseases cells and tissues by the incorporation of a specific biomarker and/or membrane protein. Antibodies, small molecules, peptides and the like can be used to target contrast agents to particular cells and/or tissues as described herein. Her-2/neu is a marker for breast cancer. A Her2/neu monoclonal antibody when conjugated to the protein polymer-based CAs aids in diagnosis and tracking of breast cancer. In contrast, previous CAs that are based on avidin/biotin interactions are limited because they need large CA concentrations to be effective in imaging, which will provoke a significant immune response.

The present invention is not limited to a particular mechanism. Indeed, an understanding of the mechanism is not necessary to practice the present invention. Nonetheless, it is contemplated that the contrast agents as described herein have high relaxivity allowing for use of smaller concentrations of the contrast agents and in some embodiments avidin and biotin are not used thereby avoiding the immune response. In some embodiments, the contrast agents are able to cross cell membranes. In some embodiments, the HIV tat peptide and polyarginine as transport peptides are incorporated into the protein polymer-Gd chelator complexes thereby allowing for the complexes to be transported across a cell membrane.

In one embodiment, the contrast agent protein polymer backbone comprises four random coil/coiled-coil block copolymers that are physically crosslinked via non-covalent intermolecular interactions of the coiled-coil domains. In some embodiments, peptide substrate sequences are incorporated between the random-coil and coiled-coil sections such that the enzyme transglutaminase (TG, for example tissue TG or tTG) is able to covalently crosslink the four protein chains into one stable complex (Hu and Messersmith, 2003, J. Am. Chem. Soc. 47:14298-14299). The present invention is not limited to a particular mechanism. Indeed, an understanding of the mechanism is not necessary to practice the present invention. Nonetheless, it is contemplated that as *E. coli* does not typically express proteins above a certain molecular weight in a high yield, forming block copolymers with the random coil and coiled coil proteins increases the concentration of Gd chelators while still maintaining an efficient synthesis strategy. It is further contemplated that this design increases the number of free lysines, and thus the number of Gd chelators, fourfold from 30 to 120 lysines.

In some embodiments, the protein polymer backbone enables both chemical coupling and enzymatic conjugation using TG to attach the Gd chelator onto the macromolecule. Chemical conjugation is less efficient in aqueous mediums and the random coil protein is water soluble. As such, it is contemplated that incorporating a hydrophobic phenylalanine residue increases the solubility of the protein in organic solvents, thereby allowing more efficient coupling reaction chemistry to obtain higher Gd coverage, further increasing image intensity. However, the present invention is not limited to the crosslinking mechanism or enzymatic conjugation method, and a skilled artisan will recognize alternative protocols and procedures equally amenable to creating the contrast agents as described herein.

The following examples are provided in order to demonstrate and further illustrate certain preferred embodiments and aspects of the present invention and are not to be construed as limiting the scope thereof.

EXAMPLES

Example 1

Protein Polymer Gd(III) Contrast Agent Complex

A multi-step controlled cloning method was used to create the gene for the protein polymer (Won and Barron, 2002, Macromolecules 35:8281). Standard transformation and expression protocols were used to produce the protein polymer (Yang et al., 2001, Tiss. Eng. 7:679). The pET19 plasmid that the gene was ligated into contains an N-terminal histidine fusion tag, $GH_{10}SSGHIDDDDKHM$ (SEQ ID NO:6), enabling protein purification via Ni-NTA affinity chromatography under denaturing conditions. Effectively, after the DNA synthesis and transformation into expression cells, the CA backbone is produced in large quantities by the bacteria and then followed with a facile purification process.

Figure 1:
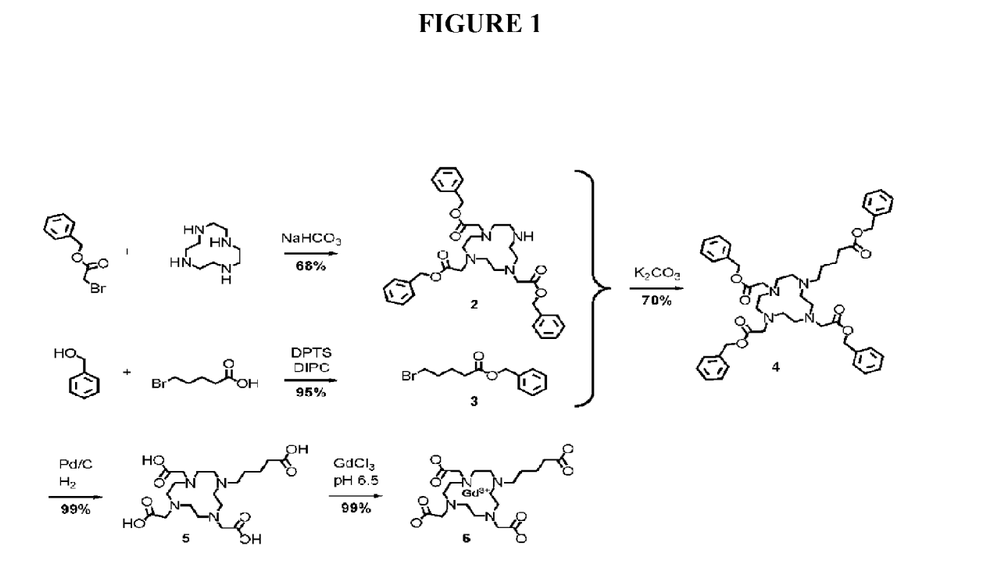
FIG. 1 demonstrated the synthesis of Gd(III) chelator using an exemplary global deprotection scheme. The Gd(III) was chelated before conjugation to the protein to ensure all chelators contained Gd(III).

A macrocyclic 1,4,7,1-tetraazacyclcododecane-1,4,7,10-tetra (acetic acid) (DOTA) derivative is used as the Gd(III) chelator. The three acetate arms chelate the Gd(III) while the carboxyl group on the 5-carbon arm is used for covalent attachment with the primary amine on the protein's lysine residues. The Gd(III) chelator was synthesized using a hydrogenation labile protection scheme with benzyl 2-bromoacetate and benzyl 5-bromopentanoate as the chelating arms of the macrocycle (FIG. 1). Addition of three benzyl 2-bromoacetate arms to cyclen was followed by addition of benzyl 5-bromopentanoate. Global deprotection by hydrogenation of the chelator and subsequent metallation with $GdCl_3$ afforded molecule Gd (III) ion 6 to be conjugated to the protein polymer.

The coupling reaction between the lysine residues on protein polymer 1 and Gd (III) ion 6 (FIG. 2), was carried out in an aqueous 0.1 M MES, 0.5 M NaCl buffer with EDC and Sulfo-NHS, peptide coupling agents. Premetallated chelators were chelated to the protein polymer in order to guarantee that every chelate had Gd(III) in it and to avoid solubility issues. Contrast agents are consistently produced that display a relaxivity of 73.4±4.1 $mM^{-1}$ $s^{-1}$ per molecule and 7.3±0.4 $mM^{-1}$ $s^{-1}$ per Gd, with a 4.5% reproducibility difference in the molecular relaxivity, with a high MRI relaxivity up to 15.6 $mM^{-1}$ $s^{-1}$ per Gd(III) and 180.3 $mM^{-1}$ $s^{-1}$ per molecule being achieved. MALDI-MS confirms ~10 lysines per molecule are being conjugated resulting in a reliable synthetic methodology.

Example 2

Hydrogel Associated Contrast Agents for Tissue Engineering

The protein polymer CAs enable the use of MRI to track tissue engineering gel scaffolds. Gels were created in 5 mm NMR for imaging. Contrast agent 7 (FIG. 2) and Gd-DTPA (a clinically used CA; Artemov et al., 2004) were doped into unconjugated protein polymer solutions and the free amines were crosslinked with glutaraldehyde to form a gel (FIG. 4). An advantage of these protein polymer-based CAs is that they covalently crosslink to assist in forming the hydrogel and can only be removed as a result of hydrolysis of the scaffold, not from diffusion. The gel with CA 7 (FIG. 2) showed dramatically higher contrast than the DTPA gel and the unconjugated protein polymer control. Although glutaraldehyde itself is toxic and other crosslinking mechanisms would be more favorable in a biological system, the results demonstrate the significant contrast enhancement and feasibility for different crosslinking reactions.

As such, the protein polymer-based CA can be incorporated into a hydrogel and display a dramatic contrast enhancement, which is important for following the evolution of the tissue engineering scaffolds.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A contrast agent comprising a chelated gadolinium and a monodisperse protein polymer, wherein said monodisperse protein polymer is in the shape of a random coil and comprises amino acid residues selected from the twenty naturally occurring amino acid residues, wherein said monodisperse protein polymer does not contain any non-naturally occurring amino acid residues, wherein said monodisperse protein polymer comprises at least two repetitive amino acid monomer units, wherein said at least two repetitive amino acid monomer units comprise lysine residues that are evenly spaced along said at least two repetitive amino acid monomer units, and wherein said lysine residues occur no more frequently than every fourth amino acid along said at least two repetitive amino acid monomer units.

2. The contrast agent of claim 1, wherein said gadolinium is gadolinium(III).

3. The contrast agent of claim 1, comprises lysine residues, wherein said lysine residues are evenly spaced along said protein polymer.

4. The contrast agent of claim 1, wherein said monodisperse protein polymer comprises the sequence GKAGTGSA (SEQ ID NO: 1).

5. The contrast agent of claim 4, wherein said monodisperse protein polymer comprises at least 30 repeats of the sequence GKAGTGSA (SEQ ID NO: 1).

6. The contrast agent of claim 1, wherein said monodisperse protein polymer is produced in bacteria.

7. The contrast agent of claim 6, wherein said bacteria is *E. coli*.

8. The contrast agent of claim 1, wherein said contrast agent is biodegradable.

9. The contrast agent of claim 1, wherein said contrast agent is cell-permeant.

10. The contrast agent of claim 1, wherein said contrast agent is non-toxic to a subject.

11. A method of magnetic resonance imaging of a subject comprising:
   a) administering a contrast agent according to claim 1 to a subject and
   b) performing magnetic resonance imaging on said subject to obtain an image.

12. The method of claim 11, wherein said subject is a mammal.

13. The method of claim 12, wherein said mammal is a human.

14. The method of claim 11, wherein said contrast agent of claim 1 comprises evenly spaced lysine residues.

15. The method of claim 11, wherein said contrast agent of claim 1 comprises the sequence GKAGTGSA (SEQ ID NO: 1).

16. The method of claim 15, wherein said contrast agent comprises at least 30 repeats of the sequence GKAGTGSA (SEQ ID NO: 1).

17. The method of claim 11, wherein said contrast agent of claim 1 is further biodegradable.

18. The method of claim 11, wherein said contrast agent of claim 1 is cell-permeant.

19. The method of claim 11, wherein said contrast agent of claim 1 is further non-toxic to a subject.

* * * * *